United States Patent

Dadinis

[11] Patent Number: 6,107,536
[45] Date of Patent: Aug. 22, 2000

[54] FLEX VENTED DOME WOUND PROTECTOR

[76] Inventor: Peter H. Dadinis, 1211 Turnbury Oak La., Houston, Tex. 77055

[21] Appl. No.: 08/858,222

[22] Filed: Apr. 28, 1997

[51] Int. Cl.$^7$ .................................................. A61F 13/00
[52] U.S. Cl. ................................. 602/41; 602/44; 602/47; 602/52; 602/58; 128/889; 128/890
[58] Field of Search ..................... 128/888, 889; 602/41–59

[56] References Cited

U.S. PATENT DOCUMENTS

| | | | |
|---|---|---|---|
| 4,285,338 | 8/1981 | Lemelson | 602/58 |
| 4,667,666 | 5/1987 | Fryslie | 128/888 |
| 4,726,364 | 2/1988 | Wylan | 602/44 |
| 4,870,977 | 10/1989 | Imonti | 128/888 |
| 4,905,681 | 3/1990 | Glascock | 128/888 |
| 4,972,829 | 11/1990 | Knerr | 602/52 |

*Primary Examiner*—Richard J. Apley
*Assistant Examiner*—Kim M. Lee

[57] ABSTRACT

A bandage that has a securing portion made of any adhesive material connected to a domed portion that is made of any rigid material that is pleated in the middle that provides shielding to protected areas from physical trauma that also flexes and allows air to flow to and from the protected area.

4 Claims, 2 Drawing Sheets

FLEX VENTED DOME WOUND PROTECTOR

CROSS REFERENCES

| U.S. Patent Documents | | | |
|---|---|---|---|
| 4,972,829 | 11/1990 | Knerr | 128/155 |
| 4,905,681 | 03/1990 | Glascock | 128/155 |
| 4,870,977 | 03/1989 | Imonti | 128/890 |
| 4,726,364 | 02/1988 | Wylan | 128/155 |

NOT SPONSORED BY ANY FEDERALLY SPONSORED RESEARCH OR DEVELOPMENT

BACKGROUND OF INVENTION

1) Field of the Invention

To provide a domed protective device for wounds, cuts, incisions or abrasions that would flex with movement, allow air flow and at the same time serve as a shield for the area to be protected.

2) Description of Related Art

| Knerr | U.S. Pat. No. | 4,972,829 |
|---|---|---|
| Glascock | U.S. Pat. No. | 4,905,681 |
| Imonti | U.S. Pat. No. | 4,870,977 |
| Wylan | U.S. Pat. No. | 4,726,364 |

The Flex Vented Dome Wound Protector provides a flexible cover which the other Patents do not.

BRIEF SUMMARY OF INVENTION

A bandage comprising a concave portion made of any rigid material that is pleated and flexible, is vented for air flow, and further comprising an adhesive portion. This invention is to provide an improved method for covering and shielding wounds, cuts, abrasions or incision during the healing process that allows the bandage to flex and also allow air to circulate to and from the area protected.

DETAILED DESCRIPTION OF THE FLEX VENTED DOME WOUND PROTECTOR

Figure 1:
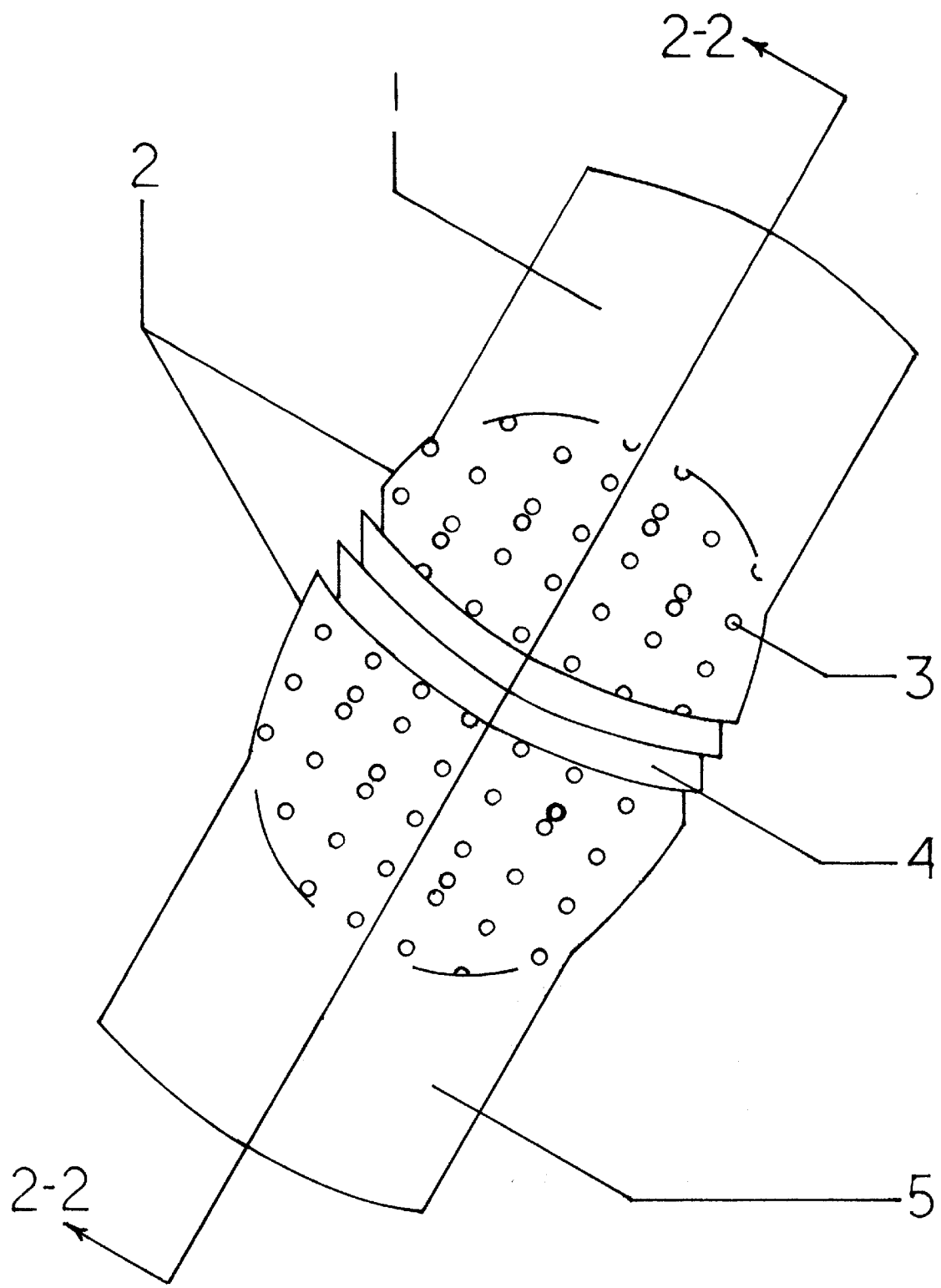
FIG. 1 is a top view of the Flex Vented Dome Protector
Figure 2:
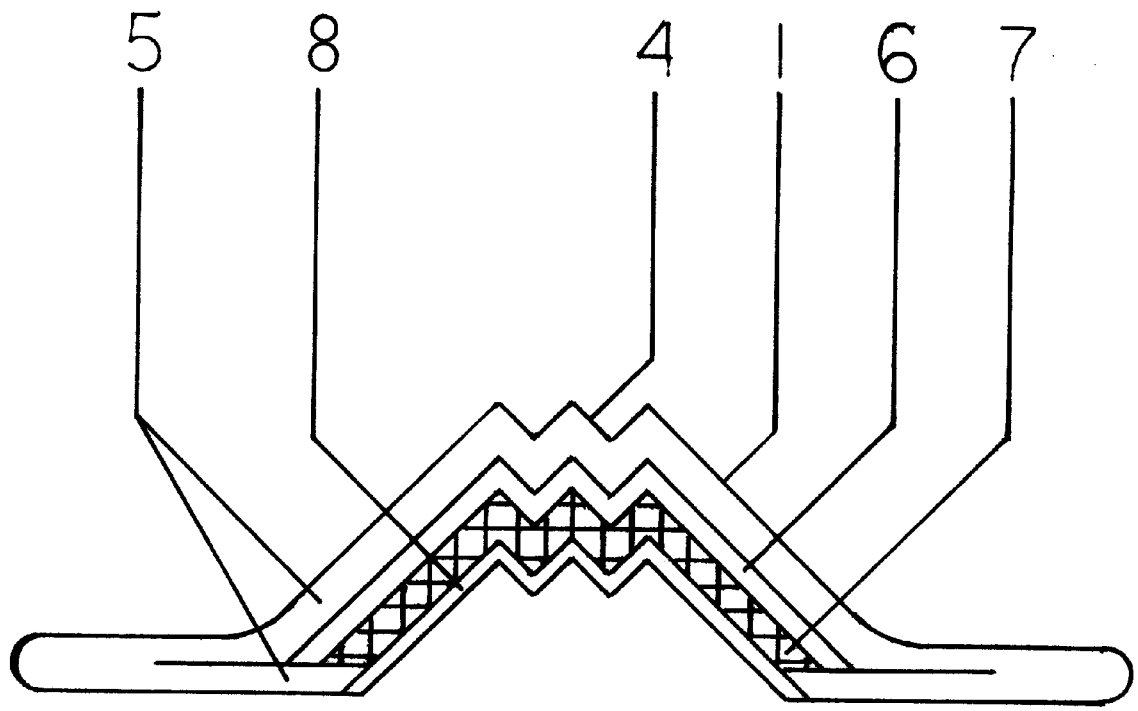
FIG. 2 is a sectional view of the Flex Vented Dome Protector

The flex vented dome wound protector (1) is shown from the top view in FIG. 1. The flex vented dome wound protector is shown in a sectional view in FIG. 2. The protector is made of four layers. The top layer (5) is made of a mesh-like material, which has elasticity, for maximum flexibility, and a skin release adhesive on its bottom side. The mesh elastic strip is perforated at the center to allow airflow to the wound. The second layer (6) a thin yet hard plastic separated into two domed halves (2) which are integrally connected with a pleated center. The second layer (6) is adhered adjacent to the adhesive side of the mesh strip. The combined width of the two halves is as wide as the plastic strip, and as long as the middle one third of the elastic mesh strip. The hard plastic dome has perforations corresponding to the perforations (3) of the adhesive mesh strip. All layers have pleats (4) in the center between the two halves to allow for stretching when the bandage is placed on a joint without disturbing the wound. The separation allows the bandage to flex and stretch so that it may be placed on joints. The flex dome concept will allow the wound to breathe and prevent disruption of the healing process by preventing the wound from being touched or disturbed by clothing or anything that might otherwise come in contact with the skin. The pleats make the bandage remarkably flexible and allows the bandage to be placed on any joint without hindering the joints flexibility. The third layer (7) is a thin air permeable gauze material to protect the wound against foreign particles that would be a risk to the wound. The word is used here to indicate any very thin, light, transparent, loosely woven material, as of cotton or silk as defined in Webster's New World Dictionary, Third College Edition's first edition. The gauze is in the same shape as the dome halves and would be adhered adjacent to the dome halves. The fourth and bottom layer (8) is a transparent non-stick material that is in the same shape as the gauze and is adhered adjacent to the layer of gauze.

I claim:

1. A pleated dome wound protector comprising:

a top material layer having a center with perforations therein to allow airflow to a wound during use, and a skin release adhesive on its bottom side;

a dome separated into two halves which are integrally connected with a pleated center, said dome is adhered to the center of the top layer on its bottom side adjacent the skin release adhesive and having perforations therein corresponding to the perforations of the top layer;

a gauze layer adhered adjacent the two dome halves, and a transparent non-stick layer adhered adjacent the gauze layer, wherein said top layer, said gauze layer, and said transparent non-stick layer are pleated at their centers between the two dome halves to allow for stretching of the protector when it is placed on a joint of a user so as not to disturb the wound or hinder joint flexibility.

2. The wound protector according to claim 1, wherein the top layer is constructed from an elastic mesh material.

3. The wound protector according to claim 1, wherein the dome is constructed from a thin yet hard material.

4. The wound protector according to claim 1, wherein the gauze layer is pleated at its center.

* * * * *